US012427061B2

(12) United States Patent
Doss

(10) Patent No.: US 12,427,061 B2
(45) Date of Patent: Sep. 30, 2025

(54) CURVED MICROTUBE FOR TREATING GLAUCOMA

(71) Applicant: R. Philip Doss, Gaviota, CA (US)

(72) Inventor: R. Philip Doss, Gaviota, CA (US)

( * ) Notice: Subject to any disclaimer, the term of this patent is extended or adjusted under 35 U.S.C. 154(b) by 687 days.

(21) Appl. No.: 17/824,789

(22) Filed: May 25, 2022

(65) Prior Publication Data

US 2023/0381020 A1    Nov. 30, 2023

(51) Int. Cl.
*A61F 9/007*    (2006.01)

(52) U.S. Cl.
CPC ................... *A61F 9/00781* (2013.01)

(58) Field of Classification Search
CPC .................................................. A61F 9/00781
See application file for complete search history.

(56) References Cited

U.S. PATENT DOCUMENTS

| 6,280,468 | B1 * | 8/2001 | Schachar | A61F 2/147 |
| | | | | 623/905 |
| 8,157,759 | B2 * | 4/2012 | Castillejos | A61F 9/00781 |
| | | | | 604/9 |
| 9,301,875 | B2 * | 4/2016 | Tu | A61F 9/00781 |
| 2012/0123438 | A1 * | 5/2012 | Horvath | A61F 9/00781 |
| | | | | 606/108 |

| 2017/0348150 | A1 * | 12/2017 | Horvath | A61L 27/222 |
| 2020/0375798 | A1 | 12/2020 | Pinchuk | |
| 2021/0267798 | A1 | 9/2021 | Kato et al. | |

FOREIGN PATENT DOCUMENTS

| SU | 1745240 A1 * | 7/1992 | ......... A61F 9/00781 |
| WO | 2014033525 A1 | 3/2014 | |
| WO | WO-2019094004 A1 * | 5/2019 | ......... A61F 9/00781 |

OTHER PUBLICATIONS

PCT/US2023/021446. International Search Report & Written Opinion (Sep. 22, 2023).

* cited by examiner

*Primary Examiner* — Leslie R Deak
(74) *Attorney, Agent, or Firm* — LOZA & LOZA, LLP; David S. Sarisky

(57) ABSTRACT

A microtube for implant into the eye includes an elongated portion and a curved portion. The elongated portion extend along a longitudinal axis and includes a distal end opening of the microtube. The curved portion is contiguous with the elongated portion and includes a proximal end opening of the microtube and a plurality of sidewall openings between the proximal end opening and the elongated portion. The curved portion curves outward relative to the longitudinal axis and back towards the distal end of the microtube. A lumen extends through the elongated portion and the curved portion between the distal end opening and the proximal end opening and is in fluid communication with the sidewall openings.

10 Claims, 11 Drawing Sheets

CURVED MICROTUBE FOR TREATING GLAUCOMA

TECHNICAL FIELD

The present disclosure relates generally to medical devices for creating fluid delivery pathways in the eye, and more particularly, to curved micro-tubes for creating drainage pathways to divert aqueous humor from the anterior chamber of the eye for treatment of glaucoma.

BACKGROUND

Glaucoma is a progressive ocular disease that manifests itself through elevated intraocular pressure (IOP). High pressure develops in an eye because of impaired outflow of aqueous humor. In open-angle glaucoma, the impaired outflow is caused by abnormalities of the drainage system of the anterior chamber. If the pressure within the eye remains sufficiently high for a long enough period of time, total vision loss occurs. Thus, glaucoma is a leading cause of preventable blindness.

SUMMARY

An aspect of the disclosure relates to a microtube for implant into the eye. The microtube includes an elongated portion and a curved portion. The elongated portion extends along a longitudinal axis and includes a distal end opening of the microtube. The curved portion is contiguous with the elongated portion and includes a proximal end opening of the microtube and a plurality of sidewall openings between the proximal end opening and the elongated portion. The curved portion curves outward relative to the longitudinal axis and back towards the distal end of the microtube. A lumen extends through the elongated portion and the curved portion between the distal end opening and the proximal end opening and is in fluid communication with the sidewall openings.

Another aspect of the disclosure relates to a method of enabling a flow of aqueous humor from the anterior chamber of an eye having a Tenon's membrane and a sclera. The method includes implanting a microtube in the eye to position a distal end opening of the microtube in the anterior chamber, and a proximal end opening of the microtube together with and a plurality of sidewall openings of the microtube in a bleb or drainage cavity in a circumferential space between the Tenon's membrane and the sclera. The implanted microtube includes an elongated portion and a curved portion. The elongated portion extend along a longitudinal axis and includes a distal end opening of the microtube. The curved portion is contiguous with the elongated portion and includes a proximal end opening of the microtube and a plurality of sidewall openings between the proximal end opening and the elongated portion. The curved portion curves outward relative to the longitudinal axis and back towards the distal end of the microtube. A lumen extends through the elongated portion and the curved portion between the distal end opening and the proximal end opening and is in fluid communication with the sidewall openings.

The microtube is designed for transconjunctival external insertion through a micro-opening puncture through the conjunctiva into the anterior chamber without the need to incise the conjunctiva. Upon implant, the proximal end of the microtube is located in a bleb or drainage cavity in a circumferential space between the Tenon's membrane and the sclera. Aqueous humor conducted by the microtube drains into the bleb. The microtube function relies on the surrounding bleb remaining open and not scarring over the microtube, which could block the outlets, e.g., the proximal end opening and the sidewall openings, of the microtube. Blocking the outlets of the microtube would prevent drainage of aqueous humor and result in elevated IOP in the eye. Insertion of the microtube without having to incise the conjunctiva decreases surgical scarring in the proximal region of the microtube having the outlets.

It is understood that other aspects of apparatuses and methods will become readily apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of apparatuses and methods will now be presented in the detailed description by way of example, and not by way of limitation, with reference to the accompanying drawings, wherein.

DETAILED DESCRIPTION

Disclosed herein is a microtube for implant into the eye includes an elongated portion and a curved portion. The elongated portion extends along a longitudinal axis and includes a distal end opening of the microtube. The curved portion is contiguous with the elongated portion and includes a proximal end opening of the microtube and a plurality of sidewall openings between the proximal end opening and the elongated portion. The curved portion curves outward relative to the longitudinal axis and back towards the distal end of the microtube. A lumen extends through the elongated portion and the curved portion between the distal end opening and the proximal end opening and is in fluid communication with the sidewall openings.

The term "distal" in this document denotes the part of the device furthest from the surgeon implanting the device. The term "proximal" denotes the part of the device closest to the surgeon implanting the device.

Microtube Configuration

Figure 1:
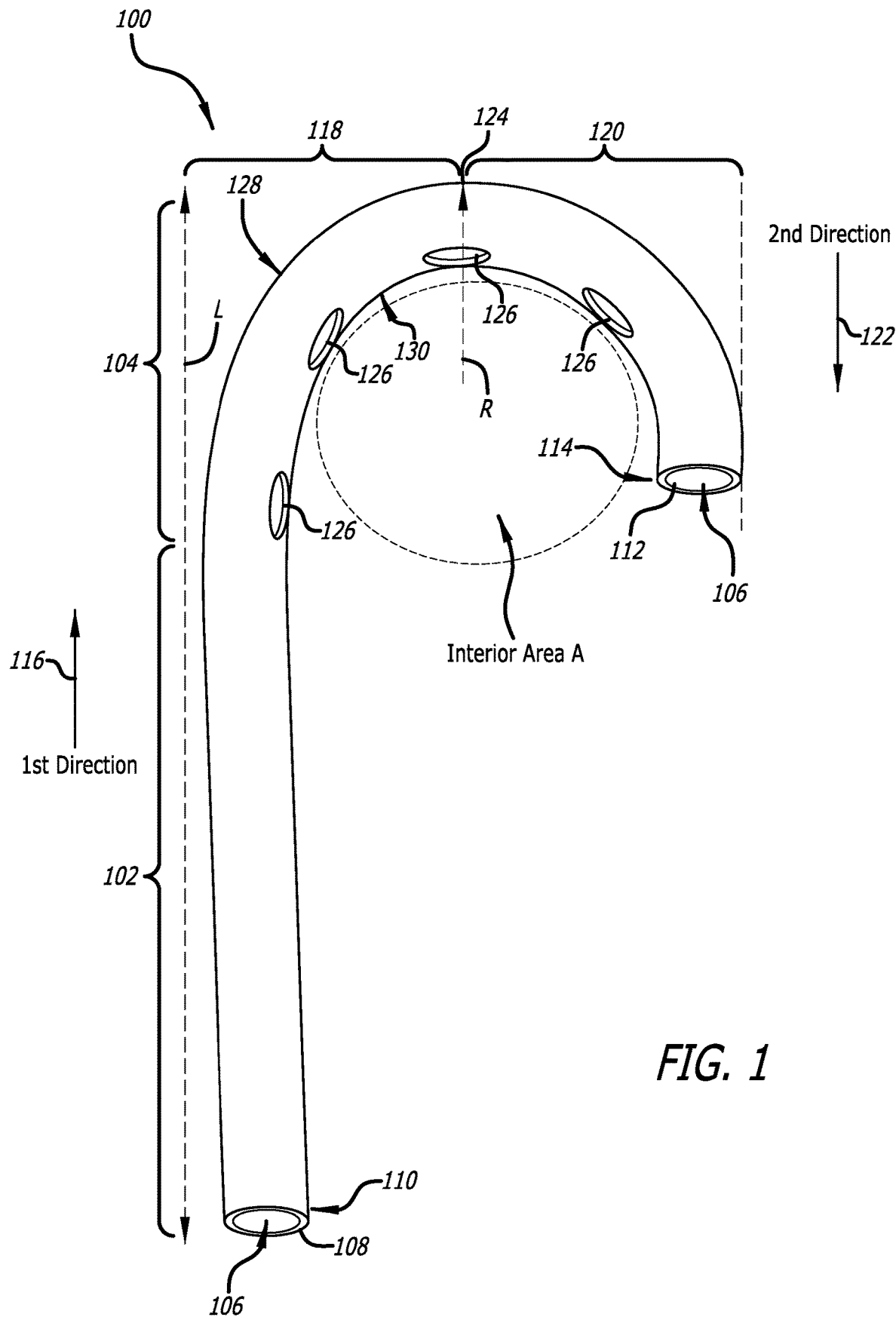
FIG. 1 is an illustration of a curved microtube with multiple sidewall openings.
Figure 2:
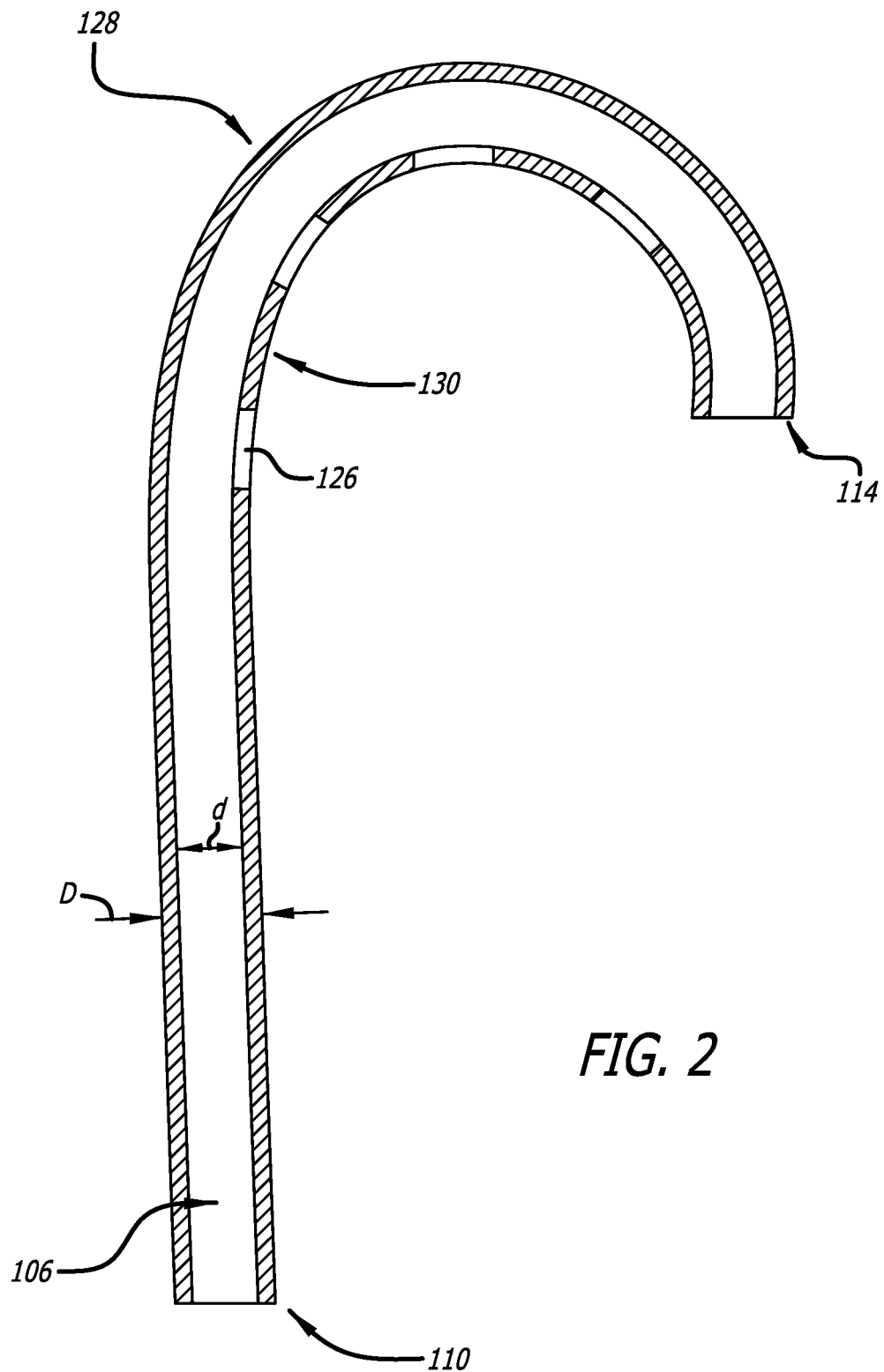
FIG. 2 is a top view of the curved microtube of FIG. 1.

With reference to FIGS. 1 and 2, a microtube 100 disclosed herein is a unitary device that can be implanted into the eye. The microtube 100 is configured to drain aqueous humor from the eye to help control elevated intraocular pressure (IOP) that can contribute to glaucoma of the eye.

The microtube 100 includes an elongated portion 102 and a curved portion 104 that define a continuous lumen 106 having a distal end opening 108 at a distal end 110 of the elongated portion and a proximal end opening 112 at a proximal end 114 of the curved portion 104. The inner diameter d of the lumen 106 can be between 40 microns (μ) and 200μ. The outer diameters D of the microtube 100 can be between 100μ and 500μ.

The elongated portion 102 forms a generally linear shape that extends along a longitudinal axis L in a first direction 116. The length of the elongated portion 102 along the longitudinal axis L may be between 8 millimeters (mm) and 12 mm.

Figure 3A:
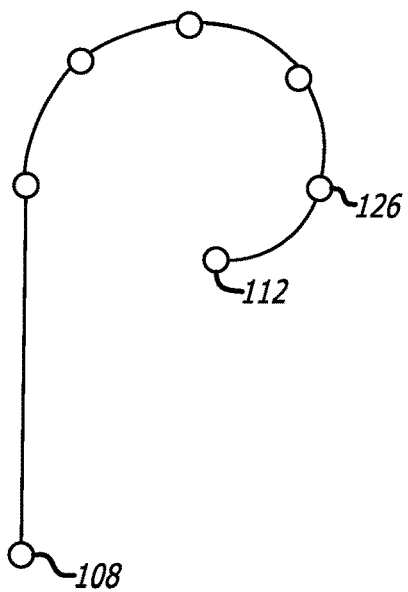
FIGS. 3A, 3B, and 3C are schematic illustrations of different shaped curved microtubes.
Figure 3B:
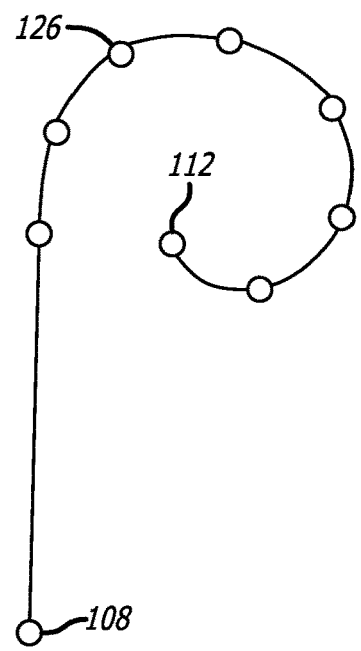
Figure 3C:
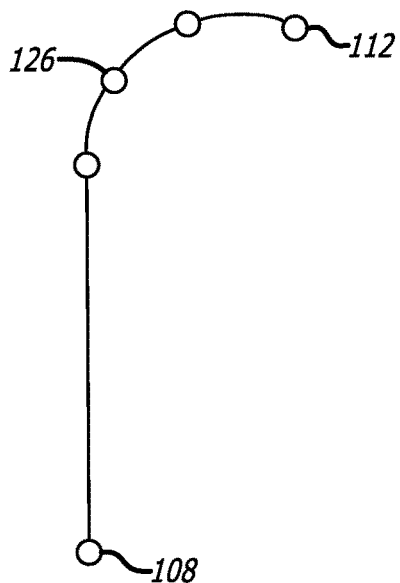

The curved portion 104 of the microtube 100 forms a semicircular shape. The curved portion 104 includes a first curved portion 118 that extends in the first direction and away from the longitudinal axis L, and a second curved portion 120 that continues the curvature of the first curved portion 118 and then continues in a second direction 122 along a longitudinal axis L opposite the first direction. The junction of the first curved portion 118 and the second curved portion 120 defines an apex 124 of the microtube 100. The radius R of the semicircular curved portion 104 shown in FIGS. 1 and 2 may be between 2 mm and 6 mm. In other configurations of the microtube 100, the curved portion 104 may have a form other than semicircular. Examples of some other curved forms are schematically shown in FIGS. 3A, 3B, and 3C.

Continuing with reference to FIGS. 1 and 2, the curved portion 104 include a plurality of sidewall openings 126. In the microtube 100 of FIGS. 1 and 2, there are four sidewall openings 126. In other configurations of the microtube 100 the number of sidewall openings may be greater or less than four. The sidewall openings 126 may be evenly spaced along the curved portion 104 beginning from the proximal end opening 112. For a curved portion 104 with a radius R between 2 mm and 6 mm the corresponding length along the semicircular curved portion is between 6.3 mm and 18.8 mm. Given these lengths, the space between adjacent sidewall openings 126 may, for example be between 1 mm (for the 6.3 mm curved portion) and 3 mm (for the 18.8 mm curved portion). The number of sidewall openings 126 may be a function of the radius R of the curved portion 104. For example, a curved portion 104 with a radius of 2 mm may have two sidewall openings, curved portion 104 with a radius of 4 mm may have four sidewall openings, and curved portion 104 with a radius of 6 mm may have six sidewall openings.

The one or more sidewall openings 126 can be defined by a respective semicircular notch or cutout in the wall of the microtube 100. The one or more sidewall openings 126 are disposed on the radially inward sidewall 130 of the microtube 100 (with respect to the lumen 106) and face an interior area A. In embodiments, the sidewall openings 126 extend diametrically through the wall of the microtube 100 from an upper surface to a lower surface of the microtube 100.

The microtube 100 can be formed from an elastomeric material that is configured to impart a normally curved shape to the curved portion 104 of the microtube, yet is flexible enough to allow the normally curved portion to assume a different, less curved shape for purposes of implanting the microtube. To this end, the microtube 100 can be formed from SIBS, which is a biocompatible, soft, atraumatic, bioinert polymer. SIBS is a polyolefinic triblock copolymer material having a triblock polymer backbone comprising poly(styrene-block-isobutylene-block-styrene). High molecular weight polyisobutylene (PIB) is a soft elastomeric material with a Shore hardness of approximately 10 A to 30 A. When copolymerized with polystyrene, it can be made at hardnesses ranging up to the hardness of polystyrene, which has a Shore hardness of 100 D. Thus, depending on the relative amounts of styrene and isobutylene, the SIBS copolymer can have a range of hardnesses from as soft as Shore 10 A to as hard as Shore 100 D. In this manner, the SIBS copolymer can be adapted to have the desired elastomeric and hardness qualities. Details of the SIBS copolymer are set forth in U.S. Pat. Nos. 5,741,331; 6,102,939; 6,197,240; 6,545,097, which are hereby incorporated by reference in their entirety.

Although SIBS is used as a preferred example, the materials used for making the microtube 100 can include silicone rubber or other suitable polymeric material. The hardness of the elastomeric polymer material of the microtube 100 can range from Shore 30 A to Shore 65 D, preferably shore 40 A to 50 A. In the event that the elongated portion 102 and curved portion 104 are formed from different polymeric materials (such as different SIBS materials), the curved portion 104 can be formed from an elastomeric polymer material (e.g., first SIBS material) with a hardness in the range of Shore 40 A to Shore 50 A, while the elongated portion 102 can be from a different elastomeric polymer material (e.g., second SIBS material) with a hardness in the range of Shore 80 A to shore 65 D and more preferably in the range of Shore 50 D to Shore 55 D.

Microtube Application

Figure 4:
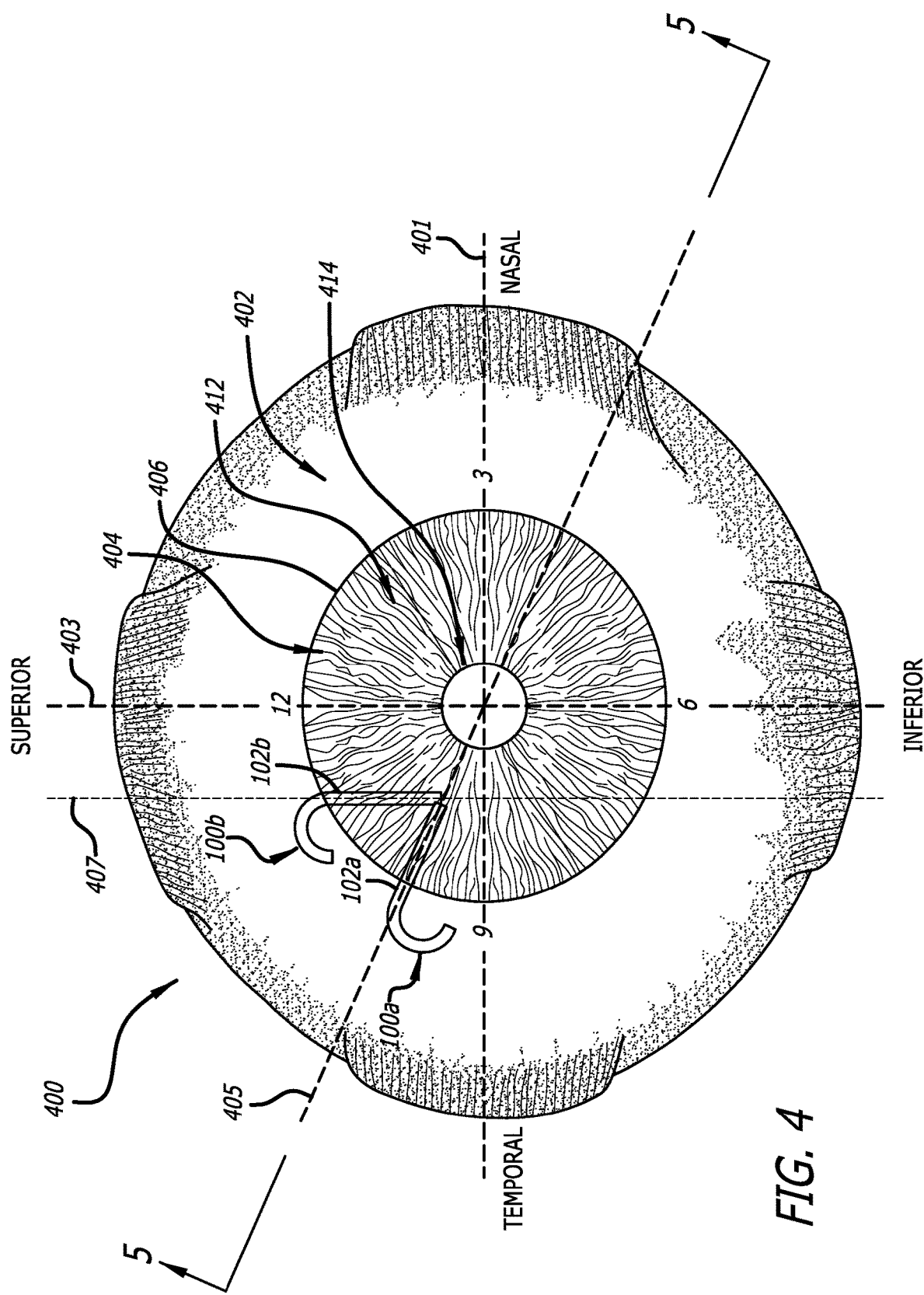
FIG. 4 is an anterior elevational view of an eye with different arrangements of implanted microtubes
Figure 5:
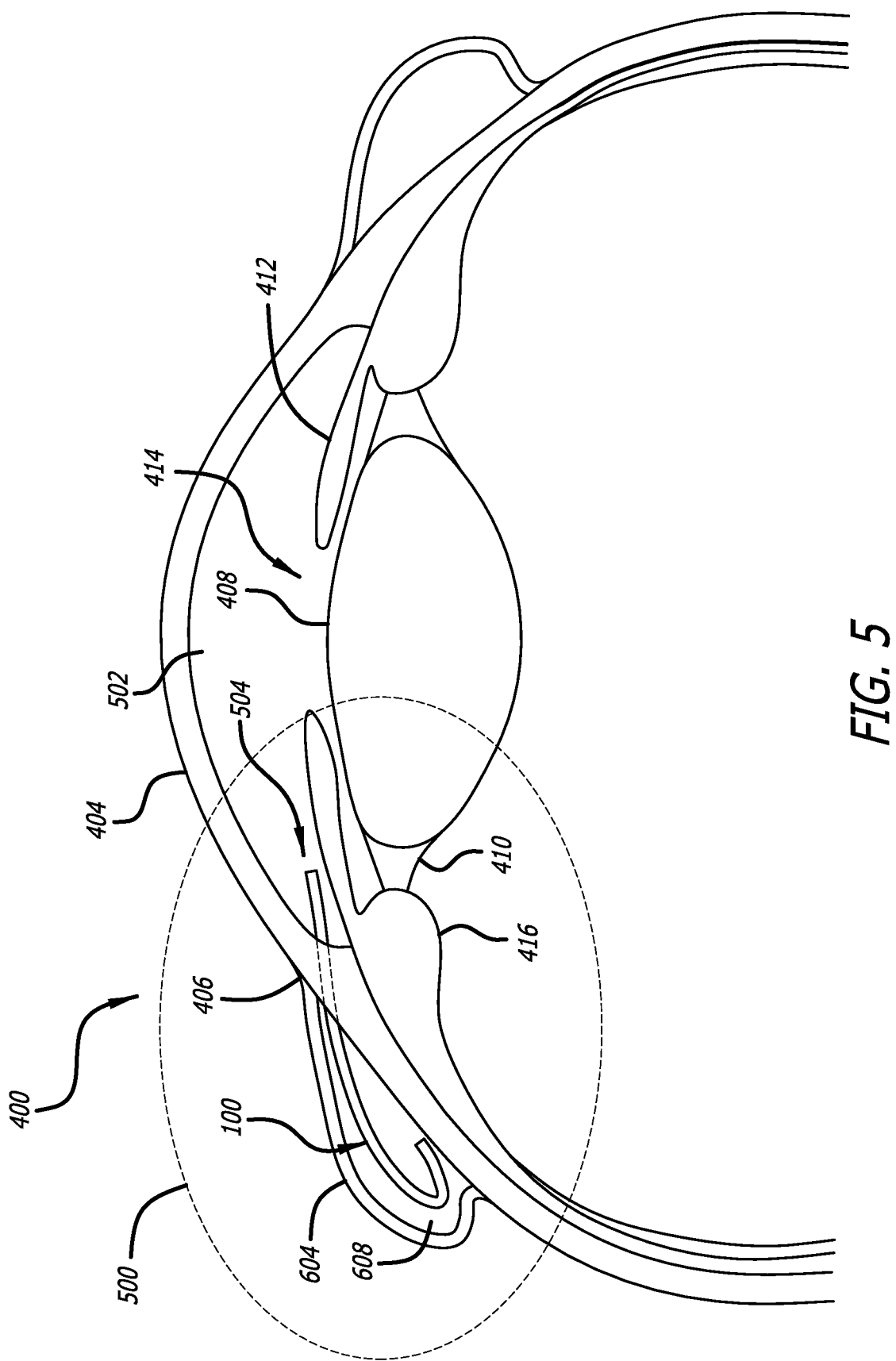
FIG. 5 is a cross-section of the eye of FIG. 4, along the line 5-5, showing an implanted microtube.
Figure 6:
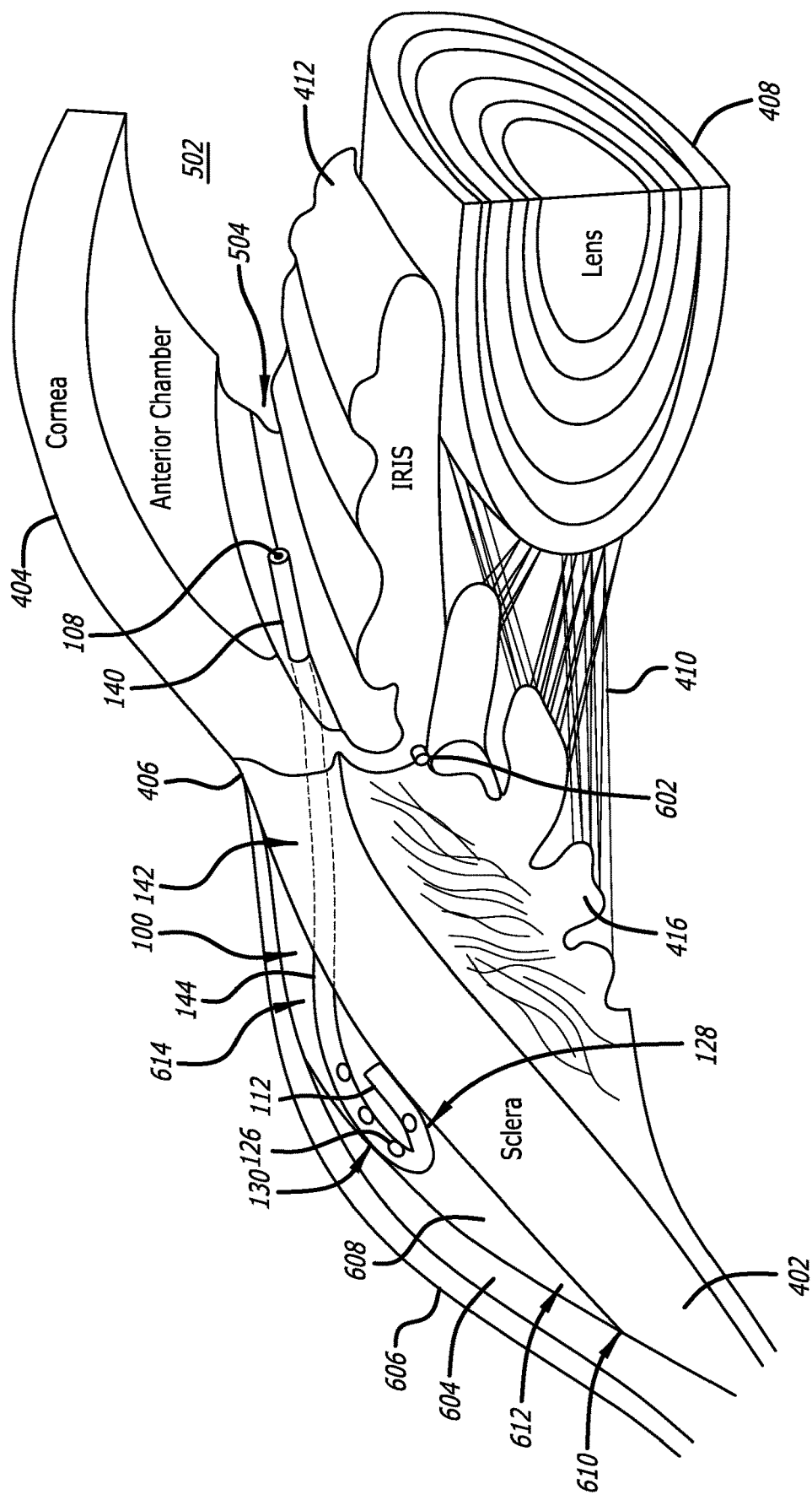
FIG. 6 is an enlarged illustration of a microtube of FIG. 5.

The relevant anatomy of the eye for implanting the microtube 100 is shown in FIGS. 4, 5, and 6. With reference to FIG. 4, which is an anterior elevational view of an eye 400, two possible implant arrangements of a microtube 100a, 100b are shown. The eye 400 may be characterized as having meridians that bisect the cornea of eye through the apex of the cornea. In FIG. 4, these meridians are described in terms of clock time, and include for example, a 3-9 o'clock meridian 401 (also referred to as a nasal-temporal meridian), and a 12-6 o'clock meridian 403 (also referred to as a superior-inferior meridian). Numerous other meridians of the eye 400 at respective clock times are present around the circumference of the cornea, however, for clarity of illustration only the nasal-temporal meridian 401 and the superior-inferior meridian 403 are shown in FIG. 4 These meridians are not anatomical features of the eye, but provide a frame of reference when describing the location of structures of the eye. FIG. 5 shows a cross-section of the eye shown in FIG. 4, along the line 5-5. FIG. 6 shows an enlarged detail of a microtubes 100 in the region defined by the circle 500 in FIG. 5.

The outermost layer of the eye 400 includes a white, tough sclera 402 which encompasses most of the globe of the eye and a transparent cornea 404. The circular junction of the cornea and sclera is a limbus 406. A portion of the sclera 402 is covered by a thin tissue called tenon's membrane 604 (also called Tenon's capsule), which envelopes the globe of the eye from the optic nerve (not shown) to the ciliary region. Near its front, Tenon's membrane 604 blends into the conjunctiva 606 where it is attached to the ciliary region of the eye as shown.

Tenon's capsule 604 is a dense, translucent, and nearly avascular fascial layer extending from the limbus 406 to the optic nerve. Anteriorly, it is located just beneath the conjunctiva 606. The conjunctiva 606 can easily be separated from the underlying Tenon's capsule 604, beginning 3 mm posterior to the limbus 406. Three millimeters posterior to the limbus 406, Tenon's capsule 604 fuses with the underlying intermuscular septum, forming a single fascial layer. Posterior to this zone, Tenon's capsule 604 envelops the globe, forming a potential cavity (sub-Tenon's space 608). This sub-Tenon's space 608, separates the Tenon's capsule 604 from the outer surface of the sclera 402. Fine bands of connective tissue link the fascial sheath to the sclera 402.

Within the globe of the eye, as illustrated in the cross-section of FIGS. 5 and 6, a crystalline lens 408 is enclosed in a thin membranous capsule and is located immediately posterior to the iris 412, suspended centrally posterior to the pupil 414 on the optical axis of the eye. The lens 408 is suspended by zonules 410 extending between the lens capsule at the equator of the lens and a ciliary body 416. The ciliary body 416 lies just under the sclera 402 (i.e., just inwardly of the sclera) and is attached to the inner surface of the sclera. The space between the cornea 404 and the lens 408 and the iris 412 defines the anterior chamber 502 of the eye 400.

With reference to FIGS. 5 and 6, the anterior chamber 502 contains a clear fluid called aqueous humor. Aqueous humor is formed by the ciliary body 416. The fluid, which is made at a fairly constant rate, then passes around the lens 408, through the pupillary opening in the iris 412 and into the anterior chamber 502. Once in the anterior chamber 502, the fluid drains out of the eye 400 through two different routes. In the uveoscleral route, the fluid percolates between muscle fibers of the ciliary body 416. This route accounts for approximately ten percent of the aqueous outflow in humans. In the canalicular route, which is the primary pathway for aqueous outflow in humans, fluid flow involves the trabecular meshwork (not shown) and Schlemm's canal 602.

The trabecular meshwork and Schlemm's canal 602 are located at the junction between the iris 412 and the sclera 402. This is typically referred to as the irido-corneal angle 504. The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal 602 is disposed adjacent to the trabecular meshwork. The outer wall of the trabecular meshwork coincides with the inner wall of Schlemm's canal 602. Schlemm's canal 602 is a tube-like structure that runs around the circumference of the cornea. In human adults, Schlemm's canal is believed to be divided by septa into a series of autonomous, dead-end canals. The aqueous fluid travels through the spaces between the trabecular beams of the trabecular meshwork, across the inner wall of Schlemm's canal 602 into the canal, through a series of collecting channels that drain from Schlemm's canal 602 and into the episcleral venous system (not shown).

In a normal patient, aqueous humor production is equal to aqueous humor outflow and intraocular pressure remains fairly constant (typically in the 8 to 18 mmHg range). In glaucoma, there is abnormal resistance to aqueous humor outflow, which manifests itself as increased IOP. In primary open angle glaucoma, which is the most common form of glaucoma, the abnormal resistance is believed to be along the outer aspect of trabecular meshwork and the inner wall of Schlemm's canal 602. Primary open angle glaucoma accounts for approximately eighty-five percent of all glaucoma. Other forms of glaucoma (such as angle closure glaucoma and secondary glaucoma) also involve decreased aqueous humor outflow through the canalicular pathway but the increased resistance is from other causes such as mechanical blockage, inflammatory debris, cellular blockage, etc.

With the increased resistance, the aqueous humor builds up because it cannot exit fast enough. As the aqueous humor builds up, the IOP within the eye increases. The increased IOP compresses the axons in the optic nerve and also may compromise the vascular supply to the optic nerve. The optic nerve carries vision from the eye to the brain. Some eyes seem more susceptible to damage from excessive IOP than other eyes. While research is investigating ways to protect the nerve from an elevated pressure, the therapeutic approach currently available in glaucoma is to reduce the intraocular pressure.

With reference to FIG. 4, in some embodiments a microtube 100a may be implanted at a superior location (above the 3-9 o'clock meridian 401) of the eye 400 and in a radial arrangement, like a spoke in a wheel, relative to the pupil 414 of the eye, or the hub of the wheel. In FIG. 4, a right eye is illustrated with the microtube 100a implanted such that the elongated portion 102a of the microtube is substantially parallel to the 4-10 o'clock meridian 405 of the eye. Substantially parallel means within 20 degrees of parallel.

In other embodiments, a microtube 100b may be implanted at a superior location of the eye 400 and in a non-radial vertical arrangement relative to the 12-6 o'clock meridian 403 of the eye. In FIG. 4, the vertically implanted microtube 100b is implanted such that the elongated portion 102b is substantially parallel to an axis 407 to the side of and parallel to the 12-6 o'clock meridian 403. The implanted microtube 100b is implanted to position the distal end of the microtube 100b near the 4-10 o'clock meridian 405 of the eye.

For clarity of illustration only one pair of microtubes 100a, 100b are shown in FIG. 4. Additional microtubes may be implanted. For example, a second microtube may be either radially or vertically implanted at a superior location of the eye 400 near the 2 o'clock position along the 4-10 o'clock meridian 405 of the eye.

With reference to FIG. 6, a microtube 100 is implanted such that its elongated portion 102 extends from the anterior chamber 502, through the sclera 402, and into a circumferential space 608 that surrounds the cornea 404, and its curved portion 104 rests entirely within the space. The circumferential space 608 extends radially outward from the limbus 406 to a posterior region 610 of the globe of eye where the Tenon's membrane 604 and the sclera 402 meet. The circumferential space 608 defines a closed space and includes an outer portion 612 between Tenon's membrane 604 and the sclera 402 and an inner portion 614 between the conjunctiva 606 and the sclera 402.

Continuing with FIG. 6, when implanted as shown, the distal end opening 108 of the microtube 100 is positioned within the anterior chamber 502 of the eye while the proximal end opening 112 and sidewall openings 126 are positioned in the circumferential space 608. The lumen 106 of the microtube 100 shunts aqueous humor from the anterior chamber 502 to the circumferential space 608. Aqueous humor exiting the microtube 100 and entering the space 608 may filter through the conjunctiva 606 into the tears or evaporate therefrom, and the fluid may be absorbed through the vascular and lymphatic systems and capillaries that interpenetrate the conjunctiva. A fraction of the aqueous humor contained in the space 608 may potentially seep through the permeable sclera 402 and be absorbed by the choroidal capillaries.

Considering the structure of microtube 100 in further detail, upon implant as shown in FIG. 6 a first section 140 of the elongated portion 102 of the microtube 100 is located in the anterior chamber 502, a second section 142 is located in the sclera 402, and a third section 144 is location in the space 608. A distal part of the third section lies in the inner portion 614 of the space 608 between the conjunctiva 606 and the sclera 402, while a proximal part of the third section lies in the outer portion 612 of the space 608 between Tenon's membrane 604 and the sclera 402. Placed as such, the proximal part of the third section 144 of the elongated portion 102 tends to position the curved portion 104 of the microtube 100 in the outer portion 612 of the space 608 between Tenon's membrane 604 and the sclera 402 instead of the inner portion 614 of the space between the conjunctiva 606 and the sclera 402.

Regarding the first, second, and third sections 140, 142, 144 of the elongated portion 102 of the microtube, in one example configuration where the elongated portion is 8 mm in length, the first section 140 of the elongated portion 102 located in the anterior chamber 502 may be approximately 2-3 mm, the second section 142 located in the sclera 402 may be approximately 2 mm, and the third section 144 located in the space 608 may be at least approximately 3 mm in order to avoid the insertion bands of Tenon's membrane 604 into the sclera 402.

With continued reference to FIG. 6, upon implant, the radially outer wall 128 of the microtube 100 faces tissue, e.g., the Tenon's membrane 604 and the sclera 402, while the radially inward sidewall 130 of the microtube faces away from the tissue. Accordingly, the sidewall openings 126 discharge fluid in a direction toward the center of the space 608 and discharge is not impeded by the tissue. Because the one or more sidewall openings 126 of the curved portion 104 are in fluid communication with the lumen 106 of the microtube 100, fluid may discharge through one or more of them. Thus, even if one of the sidewall openings 126 is closed or is blocked (such as from scar tissue overgrowth), fluid can still flow through the lumen 106 for discharge out another sidewall opening as long as the other opening is not blocked. Thus, the curved portion 104 with the plurality of sidewall openings 126 provides a redundant drainage flow path for the microtube 100, which can mitigate pressure increase in the eye that may be caused as a result of a blockage of one of the openings.

Figure 7:
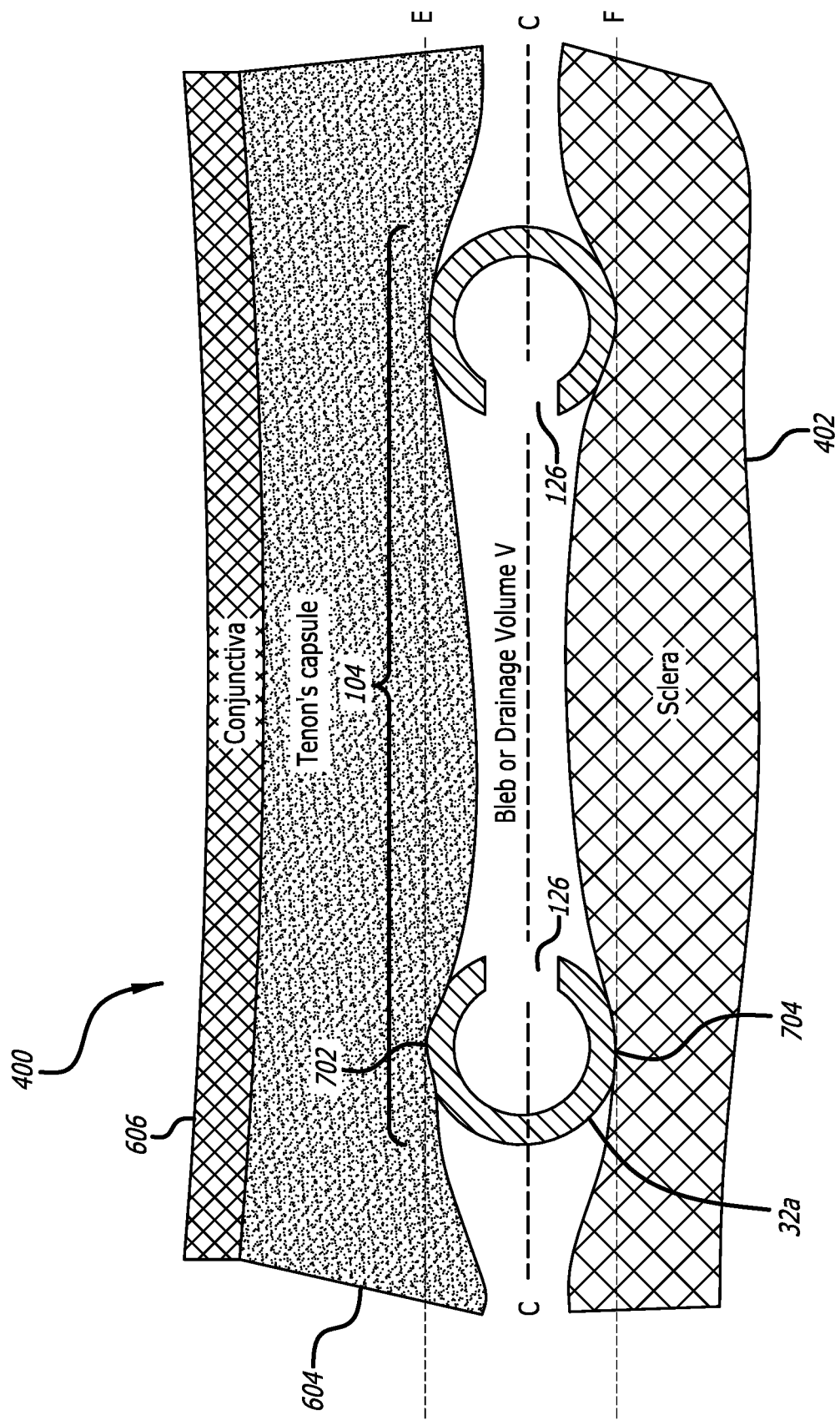
FIG. 7 is a cross-section of a portion of an implanted microtube in a space between Tenon's capsule and sclera.

As shown in the cross-sectional view of FIG. 7, the curved portion 104 can be located in a space 608 interposed between Tenon's capsule 604 and the sclera 402. In this configuration, the curved portion 104 has an upper surface 702 above axis C-C and a lower surface 704 below axis C-C. The upper surface 702 and the lower surface 704 are configured to support ocular tissue. Specifically, when implanted, the tissue of Tenon's capsule 604 can contact and interface with the upper surface 702 of the curved portion 104 and the tissue of the sclera 402 can contact and interface with the lower surface 704. When the curved portion 104 is so implanted, the surface tension of Tenon's capsule 604 and the sclera 402 may cause the surfaces of Tenon's capsule and the sclera to bow or curve inwardly toward axis C-C as shown. However, the diameter of the microtube 100 is dimensioned to maintain separation between the Tenon's capsule 604 and the sclera 402 and thereby maintain the space 608 for aqueous humor inflow.

When implanted as shown in FIG. 7, the one or more sidewall openings 126 of the curved portion 104 are in fluid communication with the space 608. The microtube 100 permits aqueous humor in the anterior chamber to flow into the distal end opening 108 through the lumen 106, and then out at least one of the sidewall openings 126 or the proximal end opening 112 and into the space 608, where the fluid can be further transported (e.g., absorbed) through the tissues adjacent the space.

Implant Methods

A microtube 100 can be implanted into the position shown in FIG. 6 utilizing a micro-opening puncture through the conjunctiva 606 that does not require suturing.

Figure 8A:
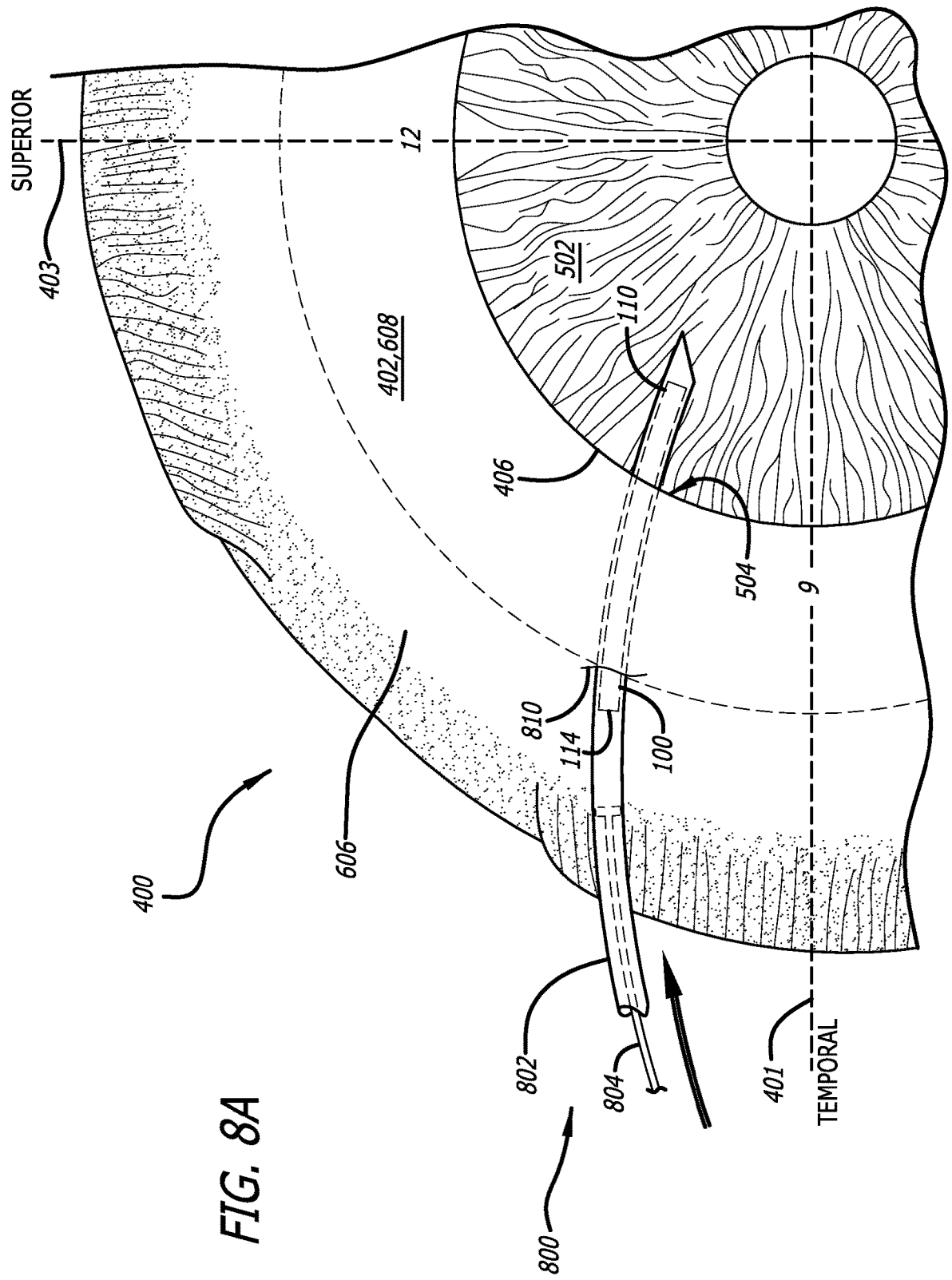
FIGS. 8A and 8B illustrate a procedure for implanting a curved microtube with a curved needle assembly.
Figure 8B:
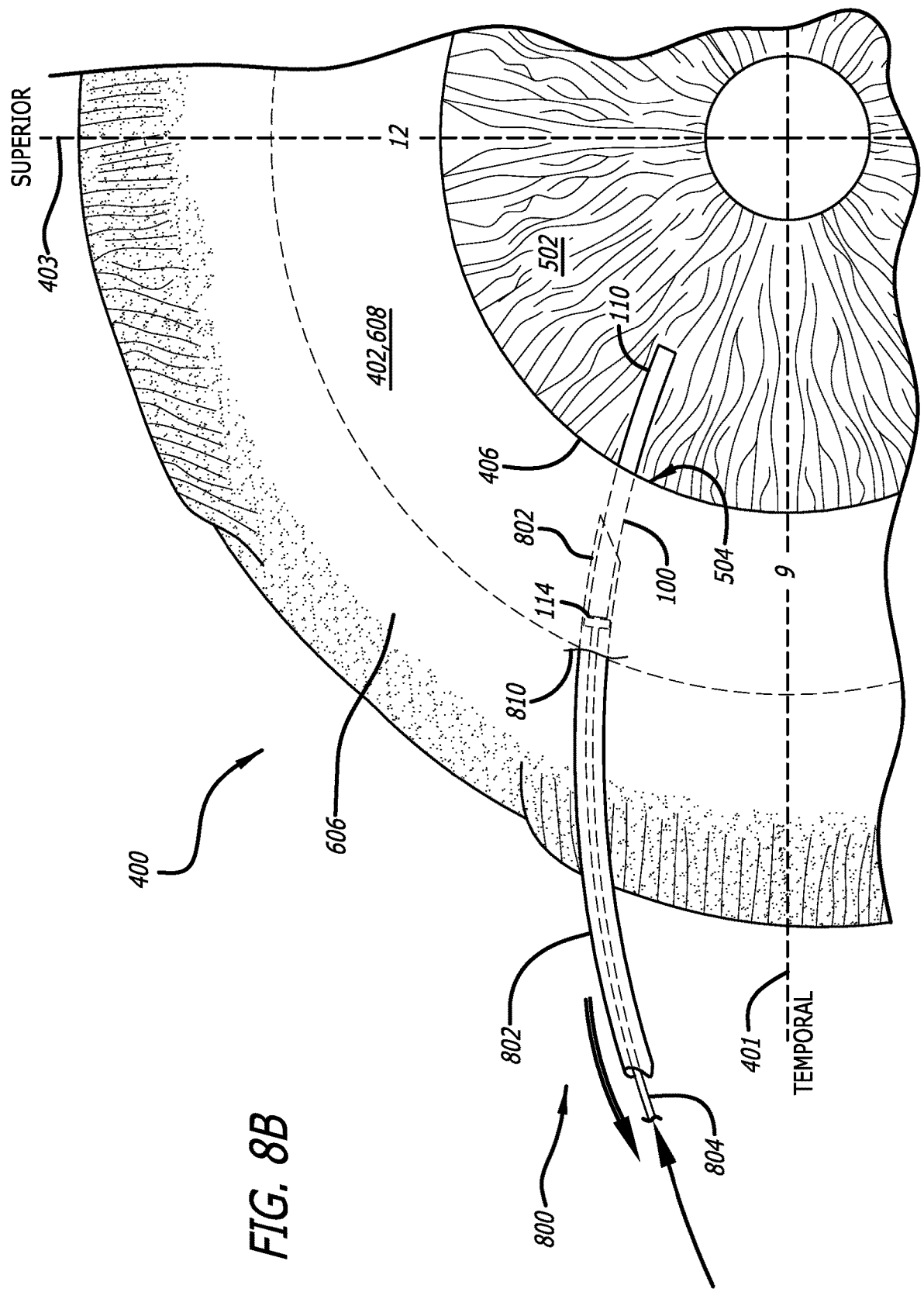

With reference to FIGS. 8A and 8B, a microtube 100 may be implanted using a curved needle assembly 800 having a hollow curved needle 802 and a plunger 804 configured to slide within the hollow curved needle. In this method, a microtube 100 is placed inside of the curved needle 802 and the tip of the needle is inserted through the conjunctiva 606 to from a micro-opening puncture 810 through the conjunctiva 606. As shown in FIG. 8A, the distal portion of the curved needle 802 is advanced through the circumferential space 608, the sclera 402, the irido-corneal angle 504 of the eye, and into the anterior chamber 502. Because the microtube 100 is inside the curved needle 802, the normally curved portion 104 of the microtube 100 transitions to match the curved shape of the needle. While a linear needle may be used, a curved needle 802 is preferred because it helps avoid anatomy that may interfere with the implant. For example, if implanting a microtube 100 from a superior approach using a linear needle, the brow of the eye may interfere. Using a curved needle enables a line of implant that avoids the brow.

With reference to FIG. 8B, the plunger 804 is arranged to push the microtube 100 in the distal direction. During implant, the plunger 804 may be pushed distally while the curved needle 802 held in place. Alternatively, the plunger 804 may be pushed distally while the curved needle 802 is being retracted from the eye through the micro-opening puncture 810. In either case, the plunger 804 is manipulated to position the proximal end 114 of the microtube 100 distal the micro-opening puncture 810 and to maintain the proximal end at that position while the tip of the curved needle is fully retracted through the micro-opening puncture.

With continued reference to FIG. 8B and additional reference to FIG. 6, with the proximal end 114 of the microtube 100 positioned distal the micro-opening puncture 810 as shown in FIG. 8B, the microtube 100 remains in place within the eye such that the elongated portion 102 of the microtube 100 extends from the space 608 through the sclera 402 into the anterior chamber 502 of the eye, while the curved portion 104 rests within the space 608. Upon retraction of the curved needle 802 through the micro-opening puncture 810, the normal curve of the microtube 100 is no longer constrained by the curved needle and due to the flexible nature of the microtube, the section of the elongated portion 102 of the microtube that is within the space 608 bends to rest on the surface of the sclera 402, while the curved portion 104 of the microtube coils into its normal curved shape, with its outer wall surfaces resting between the Tenon's membrane 604 and the sclera 402 and the sidewall openings 126 facing inward and away from tissue. Once the microtube 100 is no longer within the curved needle 802, the needle and plunger 804 are fully retracted from the eye through the micro-opening puncture 810, leaving the microtube 100 in place, such as shown in FIGS. 4, 5, and 6.

Figure 8C:
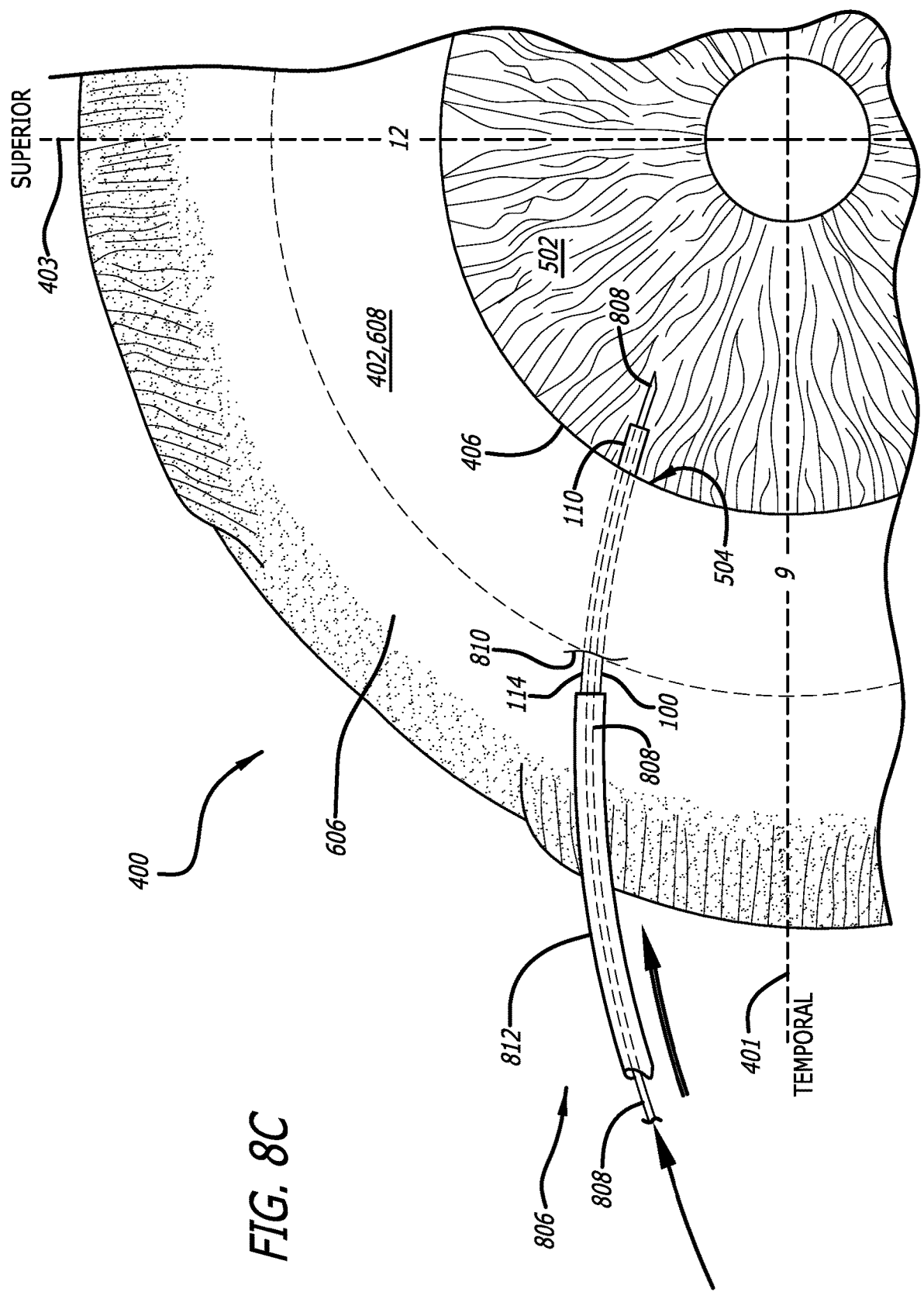
FIGS. 8C and 8D illustrate a procedure for implanting a curved microtube with a curved stylet assembly.
Figure 8D:
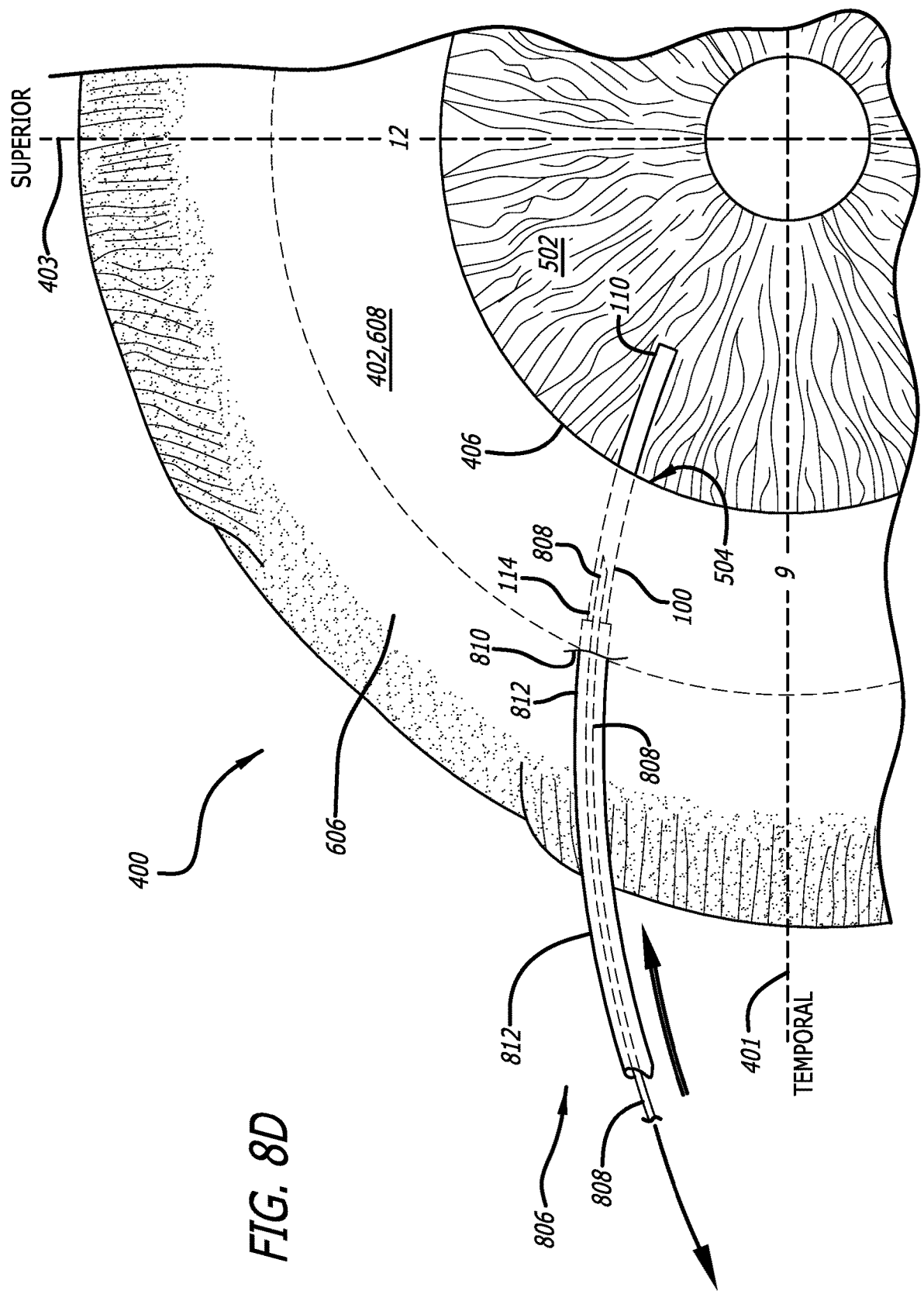

With reference to FIGS. 8C and 8D, a microtube 100 may be implanted using a curved stylet assembly 806 having a curved stylet 808 with a needle tip and a curved or pliable push tube 812. The curved stylet 808 is sized to fit within the lumen of the microtube 100 and is configured to force the curved portion of the microtube to assume the curve of the stylet. The push tube 812 is configured to slide over the curved stylet 808 and to assume the curved shape of the stylet. In this method, the curved stylet 808 is inserted through the conjunctiva 606 to from a micro-opening puncture 810 through the conjunctiva 606. As shown in FIG. 8C, the distal portion of the curved stylet 808 is advanced through the circumferential space 608, the sclera 402, the irido-corneal angle 504 of the eye, and into the anterior chamber 502. A microtube 100 is then placed over the curved stylet 808 and pushed along the length of the stylet using the push tube 812. The microtube 100 is pushed over the curved stylet 808 to place the distal end opening 108 of the microtube in the anterior chamber 502. Because the microtube 100 is over the curved stylet 808, the normally curved portion 104 of the microtube 100 transitions to match the curved shape of the stylet. While a linear stylet may be used, a curved stylet 808 is preferred because it helps avoid anatomy that may interfere with the implant. For example, if implanting a microtube 100 from a superior approach using a linear needle, the brow of the eye may interfere. Using a curved needle enables a line of implant that avoids the brow.

With reference to FIG. 8D, the push tube 812 is arranged to push the microtube 100 in the distal direction. During implant, the push tube 812 may be pushed distally while the curved stylet 808 held in place. Alternatively, the push tube 812 may be pushed distally while the curved stylet 808 is being retracted from the eye through the micro-opening puncture 810. In either case, the push tube 812 is manipulated to position the proximal end 114 of the microtube 100 distal the micro-opening puncture 810 and to maintain the proximal end at that position while the tip of the curved stylet 808 is fully retracted through the micro-opening puncture.

With continued reference to FIG. 8D and additional reference to FIG. 6, with the proximal end 114 of the microtube 100 positioned distal the micro-opening puncture 810 as shown in FIG. 8D, the microtube 100 remains in place within the eye such that the elongated portion 102 of the microtube 100 extends from the space 608 through the sclera 402 into the anterior chamber 502 of the eye, while the curved portion 104 rests within the space 608. Upon retraction of the curved stylet 808 through the micro-opening puncture 810, the normal curve of the microtube 100 is no longer constrained by the curved stylet and due to the flexible nature of the microtube, the section of the elongated portion 102 of the microtube that is within the space 608 bends to rest on the surface of the sclera 402, while the curved portion 104 of the microtube coils into its normal curved shape, with its outer wall surfaces resting between the Tenon's membrane 604 and the sclera 402 and the sidewall openings 126 facing inward and away from tissue. Once the microtube 100 is no longer over the curved stylet 808, the stylet and push tube 812 are fully retracted from the eye through the micro-opening puncture 810, leaving the microtube 100 in place, such as shown in FIGS. 4, 5, and 6.

In either of the disclosed implant methods, upon coiling of the microtube 100, the proximal end 114 of the microtube remains under the conjunctiva 606 provided the micro-opening puncture 810 is posterior enough. For example, if the microtube 100 is 8 mm in length and 3 mm of the elongated portion 102 is positioned in the anterior chamber 502 then as long as the micro-opening puncture 810 is more than 6 mm behind (or from) the limbus 406, the proximal end 114 of the microtube 100 will remain under the conjunctiva 606 and will not extend through the micro-opening puncture 810. The coiling of the microtube 100 ensures any subsequent dissection of the microtube 100 from the eye is free of fibers of the Tenon's capsule 604.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of enabling a flow of aqueous humor from an anterior chamber of an eye having a Tenon's membrane and a sclera, the method comprising:
    implanting a microtube in the eye to position a distal end opening of the microtube in the anterior chamber and a proximal end opening of the microtube in a circumferential space between the Tenon's membrane and the sclera,
    wherein the microtube comprises:
        an elongated portion extending along a longitudinal axis and including the distal end opening of the microtube;
        a curved portion contiguous with the elongated portion and including the proximal end opening of the microtube; and
        a lumen extending through the elongated portion and the curved portion between the distal end opening and the proximal end opening; wherein the eye comprises a conjunctiva, and implanting a microtube comprises:
            forming, using an instrument characterized by a curvature, a transconjunctival micro-opening puncture through the conjunctiva without incising the conjunctiva and while avoiding superior anatomy of a patient in a region of the eye; and
            inserting the microtube through the transconjunctival micro-opening puncture.

2. The method of claim 1, wherein the eye comprises a conjunctiva, and implanting a microtube comprises positioning a first section of the elongated portion in the anterior chamber, a second section of the elongated portion through the sclera, and a third section of the elongated portion in a space between the conjunctiva and the sclera without intervening Tenon's membrane.

3. The method of claim 1, wherein the instrument is formed of a material having a hardness greater than the material of the microtube such that the curved portion of the microtube assumes the curvature of the instrument.

4. The method of claim 1, wherein the instrument comprises a needle having a lumen configured to receive the microtube and inserting the microtube through the transconjunctival micro-opening puncture comprises:

inserting the microtube in the lumen of the needle;

inserting the needle with the microtube therein through anatomy of the eye to position the distal end of the microtube in the anterior chamber of the eye; and retracting the needle while maintaining the distal end of the microtube in the anterior chamber.

5. The method of claim 1, wherein the instrument comprises a stylet configured such that the microtube slides over the stylet, and inserting the microtube through the transconjunctival micro-opening puncture comprises:

inserting the stylet through anatomy of the eye to position a tip of the stylet in the anterior chamber of the eye while maintaining a portion of the stylet outside the anatomy of the eye;

pushing the microtube over the stylet to place the distal end of the microtube in the anterior chamber; and withdrawing the stylet from the lumen of the microtube while maintaining the distal end of the microtube in the anterior chamber.

6. The method of claim 1, wherein the curved portion curves outward relative to the longitudinal axis and back towards the distal end of the microtube.

7. The method of claim 1, wherein implanting a microtube in the eye comprising placing the entirety of the curved portion within the circumferential space between the Tenon's membrane and the sclera, without entering the sclera.

8. The method of claim 1, wherein the microtube comprise a plurality of sidewall openings located on an inward-facing wall of the curved portion such that the plurality of sidewall openings faces toward a central cavity of a curvature of the curved portion.

9. A method of enabling a flow of aqueous humor from an anterior chamber of an eye having a Tenon's membrane and a sclera, the method comprising:

implanting a microtube in the eye to position a distal end opening of the microtube in the anterior chamber and a proximal end opening of the microtube in a circumferential space between the Tenon's membrane and the sclera, wherein implanting the microtube comprises aligning an elongated portion of the microtube substantially parallel to a meridian of the eye, wherein the microtube comprises:

the elongated portion extending along a longitudinal axis and including the distal end opening of the microtube;

a curved portion contiguous with the elongated portion and including the proximal end opening of the microtube; and a lumen extending through the elongated portion and the curved portion between the distal end opening and the proximal end opening.

10. A method of enabling a flow of aqueous humor from an anterior chamber of an eye having a Tenon's membrane and a sclera, the method comprising:

implanting a microtube in the eye to position a distal end opening of the microtube in the anterior chamber and a proximal end opening of the microtube in a circumferential space between the Tenon's membrane and the sclera, wherein implanting the microtube comprises aligning an elongated portion of the microtube substantially parallel to an axis parallel to a 12-6 o'clock meridian of the eye, wherein the microtube comprises:

the elongated portion extending along a longitudinal axis and including the distal end opening of the microtube;

a curved portion contiguous with the elongated portion and including the proximal end opening of the microtube; and a lumen extending through the elongated portion and the curved portion between the distal end opening and the proximal end opening.

\* \* \* \* \*